United States Patent [19]

Agócs et al.

[11] Patent Number: 4,968,840
[45] Date of Patent: Nov. 6, 1990

[54] PROCESS FOR PREPARING METHOXYACETIC ACID

[75] Inventors: Pál Agócs, Veszprém; Lajos Nagy, Füzfőgyártelep; Jeno Pelyva, Füzfőgyártelep; László Légradi, Füzfőgyártelep; Zoltán Kolonics, Balatonalmádi; Csaba Söptei, Veszprém, all of Hungary

[73] Assignee: Nitrokémia Ipartelepek, Füzfőgyártelep, Hungary

[21] Appl. No.: 379,417

[22] Filed: Jul. 13, 1989

[30] Foreign Application Priority Data

Jul. 14, 1988 [HU] Hungary .............................. 18060/88

[51] Int. Cl.$^5$ .......................................... C07C 59/125
[52] U.S. Cl. .................................................. 562/588
[58] Field of Search ........................................ 562/588

[56] References Cited

U.S. PATENT DOCUMENTS 1,987,121  9/1933  Malm et al. ......................... 562/588

Primary Examiner—Paul J. Killos
Attorney, Agent, or Firm—Schweitzer Cornman & Cross

[57] ABSTRACT

A process for preparing methoxyacetic acid by reacting monochloroacetic acid with sodium methylate, in a methanolic solvent at increased temperature. Methanol is distilled off and methoxyacetic acid methylester is added to the residue. The stirrable mixture is contacted with dry hydrochloric acid gas. The methoxyacetic acid methylester is distilled off after removing the precipitated sodium chloride, to recover the desired product.

10 Claims, No Drawings

PROCESS FOR PREPARING METHOXYACETIC ACID

FIELD OF THE INVENTION

The invention relates to a process for preparing methoxyacetic acid.

BACKGROUND OF THE INVENTION

Methoxyacetic acid is an important intermediate. It is the starting material of the methoxyacetylation, namely the methoxy acetyl chloride is prepared from methoxyacetic acid, which is used in the manufacturing of plant protecting agent and pharmaceuticals. The compound can also be used as plasticizer and coloring agent, as auxiliary agent in the textile industry, and also as a flotation adjuvant.

Several processes are known for preparing methoxyacetic acid. Among these processes the following ones using monochloroacetic acid and the salt thereof as well as methanol are mentioned:

U.S. Pat. No. 2,458,741 (1949) describes a process according to which monochloro acetic acid and methanol are boiled in an autoclave for 4 hours at 200° C., when a mixture of methoxyacetic acid, methyl chloride and dimethyl ether is obtained. Yield for methoxyacetic acid is 35%.

According to German Federal Republic patent No. 2,759,169 (1979) monochloro acetic acid sodium salt, methanol, and sodium methylate are boiled for 2 hours at 75° C. then the reaction mixture is evaporated to dryness. The residue is dissolved in water, acidified with hydrochloric acid then the water is distilled off. Thereafter toluene is added to the reaction mixture and the remaining water and the excess of hydrochloric acid are distilled off. Sodium chloride is filtered hot then washed with toluene. The toluene solutions are combined and fractionated by distillation. After distilling toluene the methoxyacetic acid is purified by vacuum distillation. Yield: 85%. Disadvantages of the process are as follows:

the starting material is monochloroacetic acid sodium salt has to be prepared by a separate process;

after finishing the reaction the excess of methanol has to be distilled off, water is added to the sodium methylate and it is acidified with hydrochloric acid, then the water is distilled off. Methanol is formed from sodium methylate as a result of acidification, and in a hydrochloric acidic medium this results in ester formation with methoxyacetic acid. This compound has to be separated from water, hydrochloric acid and methoxyacetic acid;

also methoxyacetic acid is distilled off together with water, and this is difficult to recover;

dissolved sodium chloride is always present in the system due to the aqueous medium. This causes problems during distillation due to separation in the boiler.

DESCRIPTION OF THE INVENTION

It is an objective of the invention to elaborate a new simple and economical process using as starting material monochloro acetic acid, while during the process the formation of side products can be eliminated and the reagents used can be recycled to the synthesis.

The process according to the invention for preparing methoxyacetic acid involves reacting each mole of monochloro acetic acid with from about 2.2 to about 2.4 moles of sodium methylate, in the presence of a solvent optionally methanol as solvent containing methoxyacetic acid methylester, at elevated temperature, preferably at the boiling point of the reaction mixture, distilling off methanol, adding methoxyacetic acid methyl ester, reacting the stirrable mixture with dry hydrochloric acid gas, then removing the separated sodium chloride, distilling off the methoxyacetic acid methylester, and purifying the obtained methoxyacetic acid, such as by vacuum distillation.

The reaction of hydrochloric acid and methoxyacetic acid sodium salt in the anhydrous methoxyacetic methylester solvent medium is carried out at from about 20° to about 80° C. The precipitated sodium chloride is removed by filtration and washed with methanol. The methanol used for washing can contain methoxyacetic acid and methoxyacetic acid methylester. The distilled off methoxyacetic acid methylester -possibly containing free acid- can be recycled to the synthesis as a solvent.

According to the process of the present invention monochloroacetic acid is dissolved in methanol or in methoxyacetic acid methylester. The methoxyacetic acid methylester used here need not be a pure compound, it may contain monochloroacetic acid, methanol, methoxyacetic acid, for these compounds are used in the reaction.

A stoichiometric excess of sodium methylate is suitably employed. After the reaction of monochloroacetic acid is completed the methanol is distilled off, and the residue is acidified with dry hydrochloric acid gas. The precipitated sodium chloride is filtered and washed with methanol which then can be recycled to the reaction. The methoxyacetic acid methyl ester is distilled off and is also recycled to the synthesis. The residue is methoxyacetic acid of 95–98% purity, which can be further purified by vacuum distillation.

The advantages of the process of the present invention compared to the known methods include:

(1) Monochloroacetic acid is used directly as starting material and it is not necessary to prepare monochloro acetic acid sodium salt in a separate step.

(2) Methoxyacetic acid is obtained with a yield of 90% related to the monochloroacetic acid.

(3) The possibility of glycol acid formation is excluded by working in an anhydrous medium.

(4) The monochloro acetic acidic impurity of the end product is precluded by using sodium methylate in a stoichiometric excess and the reaction can be carried out completely.

(5) The technology is much simpler than that of the known processes. Equipment under pressure is not necessary as is required for example in the process of Pat. No. 2,458,741. Dilution with water by acidifying, distillation of water, and extraction with solvent as is required in Federal German patent No. 2,759,169 are all unnecessary in the present process. Additionally, the possibility of precipitation of salt is precluded, which is inevitable during distillation according to the processes using an aqueous medium.

(6) Methoxyacetic acid is present in the solvent during the entire synthesis and is not obtained by extraction; only solvent is distilled off and the loss in the product is insignificant.

(7) The process of the present invention is environmentally friendly, because the reagents do not get in contact with water, so waste-water formation is eliminated. After washing with methanol the prepared sodium chloride has a purity of over 99%, thus it is suitable for direct industrial reuse. The methanol distilling out of the system has also a purity above 99%, so it can be reused without a separate distillation step. After burning the distillation boiler residue the product is formed into he synthesis without harming the environment, because only carbon dioxide and water are formed in the burning.

(8) Sodium salt is generally used as starting material in the synthesis starting from monochloroacetic acid and it is reacted with sodium methylate. In this way one more step is necessary for preparation, as monochloroacetic acid sodium has to be prepared in a separate step, and this causes losses. If chloroacetic acid is directly used as starting material as in U.S. Pat. No. 2,458,741, then a nonuniform product is obtained with a very low yield (35%).

This disadvantage is eliminated by the process of the present invention. Monochloroacetic acid is used as starting material which obviates the need to prepare sodium salt and better yield can be achieved (90% related to monochloro acetic acid).

According to Federal German patent No. 2,759,169 acidifying is carried out in an aqueous medium by using concentrated hydrochloric acid. This is disadvantageous because methoxyacetic acid is very difficult to separate from the aqueous medium. Therefore, also on acidifying anhydrous medium is used in the present process. As, however, methoxyacetic acid methylester is formed, when methanol is treated with hydrochloric acid in an anhydrous medium, the methanol should be removed before acidifying. Methoxyacetic acid methylester is the most preferred solvent for use in the reaction with hydrochloric acid, because this dissolves the reaction partners to a satisfying extent and can then be separated from methoxyacetic acid by distillation due to its boiling point which is 70° C. lower than that of methoxyacetic acid.

EXAMPLE 1

47.25 g (0.5 mole) of monochloroacetic acid is dissolved in 200 cm$^3$ of methoxyacetic acid methylester and a methanolic solution of 200 g of 30% (1.1 mole) sodium methylate is added dropwise at 40° C. while intensely stirring. In a distillation column methanol starts to distill off slowly from the system, while 50 cm$^3$ washing methanol recycled from a previous production run, is added. The entire amount of the methanol should be removed from the system during distillation. At the end the boiler temperature is increased to at least 100° C.

The reaction mixture is then cooled and during cooling methoxyacetic acid is liberated from its sodium salt at 25°-30° C. with dry hydrochloric acid gas. The precipitated sodium chloride is filtered off. 50-100 cm$^3$ of methanol is used to wash the filtered of sodium chloride (this washing methanol is added to methanol distillation in a future production run). The methoxyacetic acid methylester solvent is distilled off from the filtrate at a pressure of about 40 bar. The residual raw product contains 95-98% of methoxyacetic acid which is further refined by vacuum distillation.

Thus 40.5 g of methoxyacetic acid is obtained, yield is 90% related to the monochloroacetic acid. The product is at least of 99% purity, the total amunt of glycolic acid and monochloroacetic acid is under 0.2%.

EXAMPLE 2

47.25 g (0.5 mole) of monochloroacetic acid is dissolved in 100 cm$^3$ of methanol and under good stirring 200 g of 30% (1.1 mole) sodium methylate is added dropwise at 40° C. The reaction mixture is then boiled. The mixture is analyzed and if the reaction has not been completed and monochloroacetic acid can be found in the reaction mixture, then further sodium methylate is added and the reaction mixture is further boiled until the complete removal of chloroacetic acid.

Thereafter the apparatus is provided with a column and the methanol is distilled off. Meanwhile the washing methanol used for washing sodium chloride in a previous production run, is added. The distillation is continued until the complete removal of methanol. The boiler temperature is then increased to at least 100° C. 200 cm$^3$ of methoxyacetic acid methylester is added to the residue and the reaction mixture is cooled. During cooling dry hydrochloric acid gas is led in at 25°-30° C. until the methoxyacetic acid is completely set free from the methoxyacetic acid sodium. The precipitated sodium chloride is filtered, washed with 50 cm$^3$ of methanol which then can be used for distillation of methanol in the next production run. The methoxyacetic acid methylester used as solvent is then stilled off, at a pressure of 40 bar. The residual raw product is of 95% purity which is further purified by vacuum distillation.

Yield is 90-91% related to monochloro acetic acid, the amount of impurities in the product is under 0.2%.

We claim:

1. A process for preparing methoxyacetic acid under substantially anhydrous conditions, which comprises reacting each mole of monochloroacetic acid with sodium methylate, distilling off methanol, adding a methoxyacetic acid methylester solvent to form a stirrable mixture of a methoxyacetic acid sodium salt, reacting the stirrable mixture with dry hydrochloric acid gas, removing the precipitated sodium chloride, and distilling off the methoxyacetic acid methylester.

2. The process of claim 1, wherein the reaction between the monochloroacetic acid and the sodium methylate is conducted at elevated temperature.

3. The process of claim 1, wherein the reaction between the monochloroacetic acid and the sodium methylate is conducted at about the boiling point of the reaction mixture, and from about 2.2 to about 2.4 moles sodium methylate is employed in said reaction.

4. The process of claim 2, further comprising purifying the methoxyacetic acid end product by vacuum distillation.

5. The process of claim 2, wherein said reaction of methoxyacetic acid sodium salt with hydrochloric acid gas is carried out at a temperature of from about 20° C. to about 80° C.

6. The process of claim 3, wherein removing the precipitated sodium chloride comprises filtering off and then washing the filtered off sodium chloride with methanol.

7. The process of claim 6, wherein the washing of the sodium chloride is carried out with a mixture of methanol containing methoxyacetic acid, and methoxyacetic acid methylester.

8. The process of claim 3, further comprising recycling the distilled off methoxyacetic acid methylester solvent which may contain free acid, to the process for reuse as solvent for the reaction between monochloroacetic acid and sodium methylate.

9. The process of claim 3, further comprising recycling the distilled off methanol to the process to the washing of the filtered off sodium chloride.

10. In a process for preparing methoxyacetic acid by reacting monochloroacetic acid and sodium methylate, distilling off methanol, and liberating with hydrochloric acid the methoxyacetic acid from its sodium salt, the improvement which comprises, reacting under substantially anhydrous conditions the monochloroacetic acid and sodium methylate in the presence of methoxyacetic acid methylester solvent at a temperature of from 40° C. to 50° C., and isolating the methoxyacetic acid thus formed.

* * * * *